Figure 1:
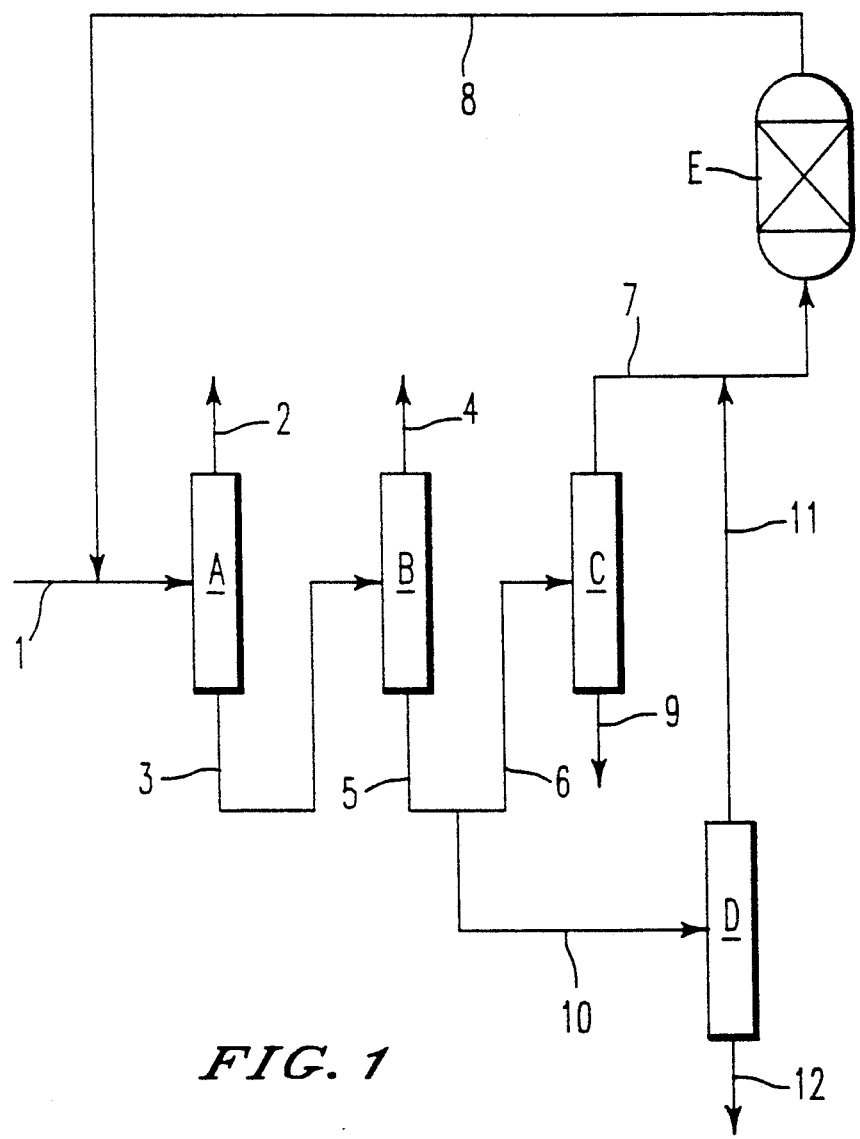

United States Patent [19]
Tan et al.

[11] Patent Number: 5,168,983
[45] Date of Patent: Dec. 8, 1992

[54] PROCESS FOR REMOVING IMPURITIES FROM THE MIXTURE OF CYCLOHEXANONE AND CYCLOHEXANOL

[75] Inventors: Kazuo Tan; Kazuhiro Fujii; Michio Nakamura, all of Kitakyushu; Kazunao Hanada, Munakata, all of Japan

[73] Assignee: Mitsubishi Kasei Corporation, Tokyo, Japan

[21] Appl. No.: 673,388

[22] Filed: Mar. 22, 1991

[30] Foreign Application Priority Data

Apr. 6, 1990 [JP] Japan .................... 2-91639

[51] Int. Cl.⁵ .................. B01D 3/14; C07C 35/08; C07C 45/82
[52] U.S. Cl. ...................... 203/29; 203/78; 203/80; 203/84; 568/366; 568/376; 568/836
[58] Field of Search ............ 203/29, 73, 78, 80, 203/84, 71; 568/366, 376, 835, 836

[56] References Cited

U.S. PATENT DOCUMENTS

| | | | |
|---|---|---|---|
| 2,873,296 | 2/1959 | Nilsson et al. | 568/835 |
| 3,275,692 | 9/1966 | Poehler et al. | 568/835 |
| 3,946,076 | 3/1976 | Paasen et al. | 568/366 |
| 4,326,085 | 4/1982 | De Cooker | 568/366 |

FOREIGN PATENT DOCUMENTS 41-19060 4/1966 Japan .................... 568/366
60-39656 9/1985 Japan .

*Primary Examiner*—Wilbur Bascomb, Jr.
*Attorney, Agent, or Firm*—Oblon, Spivak, McClelland, Maier & Neustadt

[57] ABSTRACT

A process for separating cyclohexanol and other impurities from a mixture containing cyclohexanone and cyclohexanol is disclosed. In this process a mixture of cyclohexanone and cyclohexanol are introduced into a first distillation column from which low-boiling components are distilled; the bottoms of the first distillation column are then fed to a second distillation column from which cyclohexanone is distilled; the bottoms of the second distillation column are fed to a third distillation column from which cyclohexanol and other impurities are removed; and the distillate of the third distillation column is then circulated into the first distillation column via a dehydrogenation zone; wherein the pressures at the tops of the first, second, and third distillation columns are maintained at 20 to 400 Torr; part of the bottoms of the second distillation column is supplied to a fourth distillation column having a pressure at the top of 500 to 2,500 Torr, and from which low-boiling components are removed; the distillate of the fourth distillation column is circulated into either the first distillation column, the second distillation column, the third distillation column or the dehydrogenation zone; and the bottoms of the third and fourth distillation columns are not circulated.

9 Claims, 2 Drawing Sheets

PROCESS FOR REMOVING IMPURITIES FROM THE MIXTURE OF CYCLOHEXANONE AND CYCLOHEXANOL

The present invention relates to a process for effectively separating cyclohexanol and impurities having a boiling point close to that of cyclohexanol, from a mixture containing cyclohexane and cyclohexanol prepared by oxidizing cyclohexanone.

When cyclohexanone (boiling point: 156.5° C.) and cyclohexanol (boiling point: 161° C.) are produced from cyclohexane (boiling point: 81° C.) by means of liquid phase oxidation using a molecular oxygen-containing gas, a large number of impurities are formed together with the main products, i.e., cyclohexanone and cyclohexanol.

Among major by-products formed upon the reaction are oxygen-containing compounds, such as carboxylic acids, aldehydes, ketones, esters, ethers, alcohols, etc., as well as other hydrocarbons. All of these impurities are dissolved in unreacted excess cyclohexane. Of these impurities, acidic reaction products (for example, carboxylic acids) and compounds readily soluble in water (for example, lower alcohols) can be removed therefrom by means of extraction with water. Esters and carboxylic acids not removed by the extraction are saponified with an aqueous alkaline solution and then removed. Impurities not removed by the above steps are subjected to the subsequent distillation step. Most of remaining impurities can be separated as low-boiling or high-boiling fractions since their boiling points are much different from those of cyclohexanone and cyclohexanol.

There are, however, components which are soluble to water only slightly, can be hardly saponified and having a boiling point between that of cyclohexanone and that of cyclohexanol or a boiling point very close of that of cyclohexanol. To be more specific, there are small quantity of impurities which could hardly be separated under conventional distillation conditions, that is, an overhead pressure of 20 to 400 Torr and an overhead temperature of 70° to 130° C., which conditions have been adopted in ordinary commercial production, considering various factors including cost. Typical examples of such impurities include butylcyclohexyl ether, n-pentylcyclohexane, cyclohexyl acetate, and the like.

In a known process, pure cyclohexanone is obtained from a mixture containing cyclohexanone and cyclohexanol in the following manner. At first, a first fraction containing components having a boiling point lower than that of cyclohexanone is separated by a first distillation column. Most of cyclohexanone is distilled as a second fraction out of a cyclohexanone column (second distillation column). From a third distillation column is distilled a third fraction which contains the entire cyclohexanol and the remaining cyclohexanone, as well as components having a boiling point between that of cyclohexanone and that of cyclohexanol or a boiling point very close to that of cyclohexanol. Impurities having a boiling point higher than that of cyclohexanol remain in the residue. Then, the third fraction from the third distillation column is introduced into a dehydrogenation zone, in which cyclohexanol is subjected to dehydrogenation. Cyclohexanone formed by the dehydrogenation of cyclohexanol is circulated into the first distillation column. In usual cases, the dehydrogenation is conducted in a vapor phase at a temperature of 250° to 400° C., using a catalyst containing Copper, and the conversion rate of the cyclohexanol is maintained at 60 to 80%. Under the dehydrogenation conditions, most of the impurities not separated in the above distillation steps remain unchanged. Consequently, if fractions containing such impurities are simply circulated, the impurities will accumulate in the cyclohexanone distillation system and in the dehydrogenation system. For examples, such impurities are usually present at a concentration of, at most, 100 ppm in the mixture containing cyclohexanone and cyclohexanol initially introduced into the distillation system. The concentration of the impurities increases with the progress of the circulation, and in extreme cases it rises to as high as 10% or above. In such cases, the distillation system must be stopped partly or entirely to remove the accumulated impurities out of the system. Such an interruption requires much cost and labor.

In another known process, impurities are separated by means of extraction, as disclosed in Japanese Patent Publication No. 39,656/85. This process, however, requires the use of a large quantity of solvents and hence involves considerable energy cost for the recovery of the solvents.

PROBLEMS TO BE SOLVED BY THE INVENTION

Such an increase in the quantity of impurities is inevitably accompanied by the following disadvantages.

(1) When the content of impurities contained in the cyclohexanone distillation system exceeds a certain level, it becomes difficult to separate impurities from cyclohexanone, and hence there occurs undesirable contamination of impurities, causing deterioration in the quality of purified cyclohexanone.

(2) The quantity of cyclohexanol which can be actually subjected to dehydrogenation is reduced by the presence of such impurities. In other words, the efficiency of dehydrogenation is lowered.

(3) By circulating such impurities through the cyclohexanone distillation system and the dehydrogenation zone, there is resulted an increase in heat-load required for their evaporation etc.

The present inventors have conducted detailed studies to solve the above disadvantages. As a result, it has now been found that such impurities can be removed from the cyclohexanone distillation system by drawing out the bottom of the second distillation column (which is the place where impurities having a boiling point close to that of cyclohexanone are most highly concentrated) in an amount comparable to that of impurities freshly supplied to the system; and then subjecting the separated bottom to distillation at a pressure several times to tens of times higher than that employed in the conventional distillation operation.

Accordingly, there is provided by the present invention an improvement for the above process, the gist of which is as follows:

In a process for removing impurities from a mixture containing cyclohexanone and cyclohexanol produced by oxidizing cyclohexane, comprising (a) feeding a mixture of cyclohexanone and cyclohexanol to a first distillation column in which low-boiling components are distilled off;

(b) feeding the bottoms of the first distillation column to a second distillation column in which cyclohexanone is distilled off;

(c) feeding the bottoms of the second distillation column to a third distillation column in which components consisting mainly of cyclohexanol are removed off; and (d) circulating the distillate of the third distillation column into the first distillation column via a dehydrogenation zone;

the improvement which comprises:

(e) the overhead pressure of the first, second and third distillation columns is maintained at 20 to 400 Torr;

(f) part of the bottoms of the second distillation column is supplied to a fourth distillation column of an overhead pressure of 500 to 2,500 Torr, in which lower-boiling components are removed off;

(g) the distillate of the fourth distillation column is circulated into at least one of the steps selected from the group consisting of the first distillation column, the second distillation column, the third distillation column and the dehydrogenation zone; and (h) the bottoms of the third and fourth distillation columns are removed from the circulation system.

In FIG. 1 is shown a flow chart of an embodiment of the present invention. In the figure, A indicates a first distillation column, B indicates a second distillation column, C indicates a third distillation column, D indicates a fourth distillation column, and E indicates a dehydrogenator.

The present invention will further be illustrated according to FIG. 1.

A mixture containing cyclohexanone and cyclohexanol is supplied to the first distillation column A via a feeding pipe 1, and the product from the dehydrogenator E is circulated into the same column. The low-boiling overhead product of the distillation column A is removed via a pipe 2. On the other hand, the bottoms of the column A is taken out via a pipe 3 and supplied to the second distillation column B.

In the distillation column B, cyclohexanone is distilled off from the top of the column via a pipe 4. On the other hand, the bottoms of the column B is taken out via a pipe 5 and supplied to the third distillation column C via a pipe 6.

In the distillation column C, an overhead product consisting mainly a cyclohexanol is taken out, and the product is supplied to the dehydrogenator E.

The reaction product from the dehydrogenator E is circulated via the pipe 8 into the first distillation column.

The distillation columns A, B and C are operated at an overhead pressure of 20 to 400 Torr, preferably highest in the column A and lowest in the column C. For example, the column A is operated at an overhead pressure of 200 to 400 Torr, the column B at 50 to 200 Torr. and the column C at 20 to 100 Torr. The overhead temperature is controlled in accordance with the overhead pressure, usually in the range of 70° to 130° C.

The high-boiling bottom product of the distillation column C is taken out of the circulation system via a pipe 9.

Part of the bottoms from the distillation column B is supplied to the fourth distillation column D via a pipe 10. The bottoms of the column B is supplied to the column D in an amount comparable to that of impurities freshly circulated or accumulated into the system, which is usually of 0.1 to 10%, preferably 0.5 to 3% of the total weight of the bottoms B.

The distillation column D is operated at an overhead pressure of 500 to 2,500 Torr, preferably 600 to 1,000 Torr, most preferably at around atmospheric pressure. The impurities can be separated by operating the distillation column D at an overhead pressure of 500 to 2,500 Torr, which is higher than the overhead pressure of 20 to 400 Torr at which the distillation columns A, B and C are operated. When the column D is operated at an overhead pressure lower than 500 Torr, there will be resulted in an insufficient separation of the impurities, whereas when it is operated at an overhead pressure above 2,500 Torr, the distillation temperature will exceed the temperature range ordinarily employed in commercial operations and, in addition, there will be resulted an undesirable acceleration of resinification due to the high temperature in the column. In usual cases, the overhead temperature of the distillation column D is controlled at a temperature in the range of 150° to 220° C., depending on the overhead temperature of the column.

The distillate of the distillation column D is supplied to the dehydrogenator E, together with the distillate from the distillation column C, whereas the bottoms of the column D is taken out of the circulation system via a pipe 12. If desired, the distillate of the distillation column D can be directly circulated into the column A, B or C, although it is preferred to circulate it into the dehydrogenator E as shown in FIG. 1 since the distillate is consisted mainly of cyclohexanol.

EXAMPLES

The present invention will be illustrated in more detail by the following examples. It should however be understood that the scope of the invention is by no means limited to these.

Example 1

This operation was carried out according to the flow chart shown in FIG. 1.

A mixture containing cyclohexanone and cyclohexanol obtained by oxidizing cyclohexanone was combined with the product circulated from the dehydrogenator E, and the resulting mixture (cyclohexanone, 36%; cyclohexanol, 53%) was supplied to the first distillation column A at a rate of 100 parts/Hr. After low-boiling components had been distilled off at an overhead pressure of 200 Torr and a reflux ratio of 20, the bottoms of the column A was supplied to the second distillation column B at a rate of 99.3 parts/Hr. The column B was operated at an overhead pressure of 50 Torr and a reflux ratio of 4 to recover cyclohexanone at a rate of 33.5 parts/Hr. On the other hand, its bottoms (cyclohexanone, 3%; cyclohexanol, 81%) was supplied to the third distillation column C at a rate of 65.1 parts/Hr. The column C was operated at an overhead pressure of 30 Torr and a reflux ratio of 2 to remove high-boiling components contained in the bottoms of the column B at a rate of 1.2 parts/Hr. The distillate of the column C was introduced at a rate of 64.6 parts/Hr. into the dehydrogenator E charged with a catalyst containing Copper. The dehydrogenation of cyclohexanol was conducted in a vapor phase at 250° C., and the resultant reaction product was circulated into the first distillation column A.

About 1% of the bottoms of the second distillation column B was supplied to the fourth distillation column D at a rate of 0.7 parts/Hr., and the column D was operated at a pressure of 760 Torr (i.e., atmospheric pressure) and a reflux ratio of 5. Impurities (i.e., the bottoms of the column D) were removed at a rate of 0.1 parts/Hr., and its distillate was supplied to the dehydrogenator E at a rate of 0.6 parts/Hr.

The distillation system reached a stationary state after 100 days from the beginning of the operation. In the stationary state, the reaction mixture from the dehydrogenator E had the following composition:

| Cyclohexanone | 60% |
|---|---|
| Cyclohexanol | 37% |
| Impurities | 3% |

In Table 1 are shown compositions in the stationary state of the bottoms of the distillation column B, and of the bottoms and the distillate of the distillation column D.

TABLE 1

| | Bottoms of Distillation Column B (wt %) | Distillate of Distillation Column D (wt %) | Bottoms of Distillation Column D (wt %) | Impurity Removal Rate (%)*3 |
|---|---|---|---|---|
| N + L*1 | 92.5 | 99.0 | 1.5 | |
| Impurities*2 | 6.0 | 1.0 | 76.0 | 85.0 |
| Others | 1.5 | 0.0 | 22.5 | |

[Note]
*1Total percentage of cyclohexanone and cyclohexanol
*2Total percentage of the following impurities:
 Butylcyclohexyl ether
 n-pentylcyclohexane
 Cyclohexyl acetate

*3Impurity removal rate (%) =

$$\left(1 - \frac{\text{Ratio of [*2] to [*1] in Distillate of Distillation Column D}}{\text{Ratio of [*2] to [*1] in Bottoms of Distillation Column B}}\right) \times 100$$

Comparative Example 1

Figure 2:
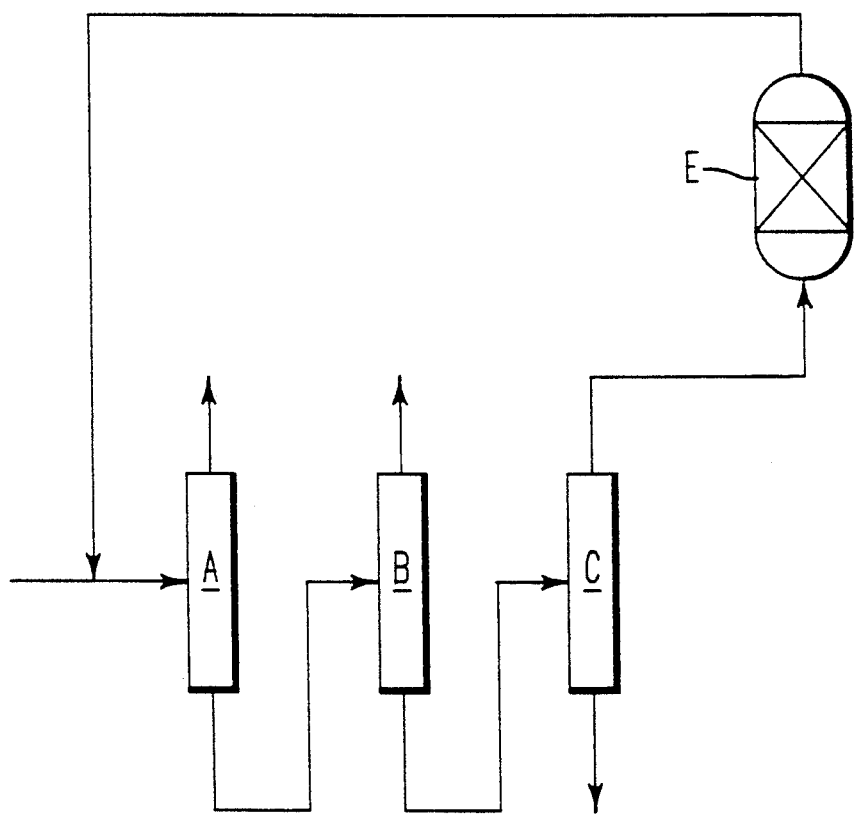

This operation was carried out according to the flow chart shown in FIG. 2.

FIG. 2 is a flowchart showing an embodiment of Comparative Example 1, wherein A indicates a first distillation column; B, a second distillation column; C, a third distillation column; and E, a dehydrogenator.

In the figure, A indicates a first distillation column, B indicates a second distillation column, C indicates a third distillation column, and E indicates a dehydrogenator. This distillation system is identical with that shown in FIG. 1, except that the branch-flow into the fourth distillation column D is omitted.

The columns A to C and the dehydrogenator E were operated under the same conditions as in Example 1. The distillation system reached a stationary state after 150 days from the beginning of the distillation. In the stationary state, the reaction mixture from the dehydrogenator E had the following composition:

| Cyclohexanone | 53% |
|---|---|
| Cyclohexanol | 32% |
| Impurities | 15% |

Example 2

This operation was carried out according to the flow chart shown in FIG. 1 under the same conditions as in Example 1, except that the overhead pressure of distillation column D was set at 1,000 Torr.

In the stationary state, the hydrogenated product from the dehydrogenator had the following composition.

| Cyclohexanone | 61% |
|---|---|
| Cyclohexanol | 37% |
| Impurities | 2% |

Comparative Example 2

This operation was carried out according to the flow chart shown in FIG. 1 under the same conditions as in Example 1, except that the overhead pressure of the distillation column D was set at 300 Torr.

During the operation, no impurities were separated by the distillation column D. The concentration of impurities contained in the reaction product from the dehydrogenator exceeded 10% in 100 days after the beginning of the distillation.

MERITS OF THE INVENTION

The level of impurities circulated and accumulated in the system for distilling and dehydrogenating cyclohexanone can be lowered, and this lowering in the impurity level enables to lower the level of impurities in the distilled cyclohexanone. It is possible to produce cyclohexanone in larger quantities even when a dehydrogenator having the same liquid hourly space velocity (LHSV) is used, since the quantity of cyclohexanol feedable to the dehydrogenator increases due to the lowering in the level of impurities into the dehydrogenator. It is also possible to reduce the heat-load, or energy required to circulate impurities through the distillation and dehydrogenation system. Since cyclohexanone and cyclohexanol have been produced in considerably large quantities, the present process can be of great value from industrial point of view.

We claim:

1. In a process for removing impurities from a mixture containing cyclohexanone and cyclohexanol produced by oxidizing cyclohexane, comprising
  (a) feeding a mixture of cyclohexanone and cyclohexanol to a first distillation column from which mixture low-boiling components are distilled;
  (b) feeding a bottoms of the first distillation column to a second distillation column from which cyclohexanone is distilled;
  (c) feeding a bottoms of the second distillation column to a third distillation column from which components consisting mainly of cyclohexanol are distilled; and
  (d) circulating a distillate of the third distillation column into the first distillation column via a dehydrogenation zone; wherein each of said first, second, and third distillation columns possesses a top;
wherein the improvement comprises:
  (e) a pressure at each of said tops of the first, second and third distillation columns is maintained at 20 to 400 Torr;
  (f) part of the bottoms of the second distillation column is supplied to a fourth distillation column possessing a top having a pressure at said top of 500 to 2,500 Torr, from which low-boiling components are removed;
  (g) a distillate the fourth distillation column is circulated into at least one of the components selected from the group consisting of the first distillation column, the second distillation column, the third distillation column and the dehydrogenation zone; and (h) a bottoms of the third distillation column and a bottoms of the fourth distillation column are not circulated.

2. The process according to claim 1, wherein the pressure at said top is highest in the first distillation column and lowest in the third distillation column.

3. The process according to claim 1, wherein the first distillation column is operated at a pressure at said top of 200 to 400 Torr, the second distillation column at 50 to 200 Torr, and the third distillation column at 20 to 100 Torr.

4. The process according to claim 1, wherein a temperature at each of said tops of the first, second, and third distillation columns is 70° to 130° C.

5. The process according to claim 1, wherein 0.1 to 10 percent by weight of the bottoms of the second distillation column is supplied to the fourth distillation column.

6. The process according to claim 1, wherein the distillate of the fourth distillation column is supplied to the dehydrogenation zone, together with the distillate from the third distillation column.

7. The process according to claim 1, wherein the pressure at said top of the fourth distillation column is 600 to 1,000 Torr.

8. The process according to claim 1, wherein the temperature at said top of the fourth column is 150° to 220° C.

9. The process according to claim 1 wherein the dehydrogenation is carried out in vapor phase using a fixed bed catalyst containing copper in the dehydrogenation zone.

* * * * *